United States Patent [19]

Kralovic

[11] Patent Number: 5,863,499
[45] Date of Patent: Jan. 26, 1999

[54] LIGHT WEIGHT VENTED PACKAGE FOR LIQUIDS

[75] Inventor: Raymond C. Kralovic, Hambden, Ohio

[73] Assignee: Steris Corporation, Mentor, Ohio

[21] Appl. No.: 963,400

[22] Filed: Nov. 3, 1997

[51] Int. Cl.[6] .................................................. A61L 11/00
[52] U.S. Cl. .................... 422/32; 422/184.1; 422/286; 422/292; 422/309; 426/487; 53/451; 53/410; 53/449; 53/381.2; 53/492; 53/474; 53/239; 53/237; 493/210; 493/929; 493/932; 493/934; 206/439; 383/907; 383/100; 436/297.5
[58] Field of Search .......................... 422/28, 32, 184.1, 422/286, 292, 294, 309; 426/486, 487; 53/451, 410, 434, 449, 381.2, 492, 474, 445, 238, 239, 237; 206/569, 439; 383/100, 103, 907, 101, 104; 436/297.5, 304.1; 493/210, 934, 932, 929

[56] References Cited

U.S. PATENT DOCUMENTS

| | | | |
|---|---|---|---|
| 3,026,658 | 3/1962 | Schneider et al. | 53/451 |
| 3,529,397 | 9/1970 | Leasure | 53/451 |
| 3,925,959 | 12/1975 | Dykes et al. | 53/451 |
| 4,578,185 | 3/1986 | Wilson, et al. | 210/85 |
| 4,618,103 | 10/1986 | Wilson, et al. | 241/41 |
| 4,619,409 | 10/1986 | Harper, et al. | 241/38 |
| 5,037,623 | 8/1991 | Schneider, et al. | 422/292 |
| 5,054,696 | 10/1991 | Mennel, et al. | 241/34 |
| 5,089,228 | 2/1992 | Meijer | 422/37 |
| 5,553,942 | 9/1996 | Domke et al. | 383/103 |

FOREIGN PATENT DOCUMENTS 1304099  12/1962  France .

OTHER PUBLICATIONS

"Desinfectant Effect of Persteril In Combination With Detergents/", V. Melicherčiková, Journal of Hygiene, Epidermiology, Microbiology and Immunology, 33, 1989, No. 1, 19–28.

"Studies Concerning the Mechanism of Bleaching Activation", Hauthal, et al. Tenside Surf. Det. 27 (1990) 3, pp. 187–193.

"Effect of pH on Sproicidal and Microbicidal Activity of Buffered Mixtures of Alcohol and Sodium Hypochlorite", Death, et al., J. of Clinic Pathology 1979, 32 148–153.

Primary Examiner—Krisanne Thornton
Assistant Examiner—Fariborz Moazzam
Attorney, Agent, or Firm—Fay, Sharpe, Beall, Fagan, Minnich & McKee

[57] ABSTRACT

A self-venting package (A) contains peracetic acid or other strong oxidants in a unit dose that assures sterilization of instruments and equipment in an automated sterilizing apparatus (FIG. 3) or of biological wastes in a biological waste comminuting apparatus (FIG. 4). The self-venting package is constructed of a cylindrical body having first and second vent apertures (12, 14) 180° offset adjacent a first edge (20) and third and fourth vent apertures (16, 18) 180° offset adjacent a second edge (26). The first and second vent apertures are 90° offset relative to the third and fourth vent apertures. The first edge is flattened and sealed forming a pair of corners (40, 42) such that the first and second vent apertures are disposed closely adjacent the first and second corners. The container is filled with peracetic acid or other liquids which liberate gas or vapors. A second end (26) of the container is flattened and sealed in a direction transverse to the first edge. Flattening the second edge defines third and fourth corners (44, 46). The third and fourth vent apertures are disposed closely adjacent to the third and fourth corners. Portions of a semi-permeable membrane (32, 34, 36, 38) cover each of the vent apertures. The semi-permeable membrane permits gas or vapor to pass freely therethrough while blocking the passage of liquids.

20 Claims, 5 Drawing Sheets

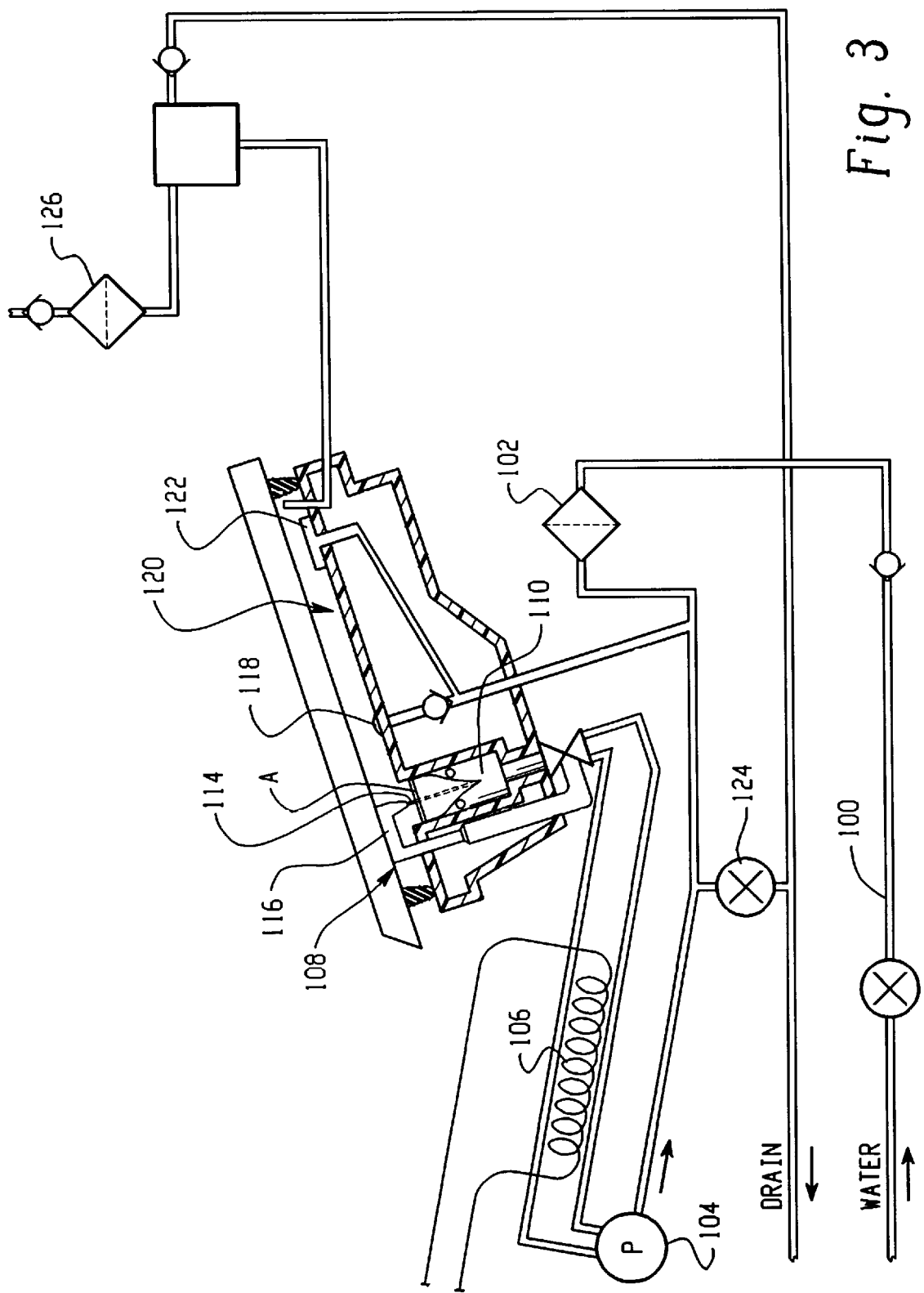

LIGHT WEIGHT VENTED PACKAGE FOR LIQUIDS

BACKGROUND OF THE INVENTION

The present application relates to microbial decontamination arts. It finds particular application in conjunction with the sterilizing or disinfecting of medical, dental, surgical, mortuary, laboratory, and other equipment which comes in contact with the human body, particularly the interior of the human body. The invention also finds particular application in conjunction with the sterilizing or disinfecting of medical wastes as well as disposable medical equipment which has come into contact with the interior of the human body. It is to be appreciated, however, that the present invention will also find application in conjunction with the packaging and use of other liquids which outgas or emit gas or vapor during storage and shipment.

Heretofore, medical facilities have commonly used steam autoclave sterilization systems. Instruments and equipment to be sterilized or disinfected were transported to a central sterilizing facility where they were sterilized under the supervision of sterilizing room technicians. In a steam autoclave, which typically has a cycle time of one to two hours, the equipment was subject to superheated steam at high pressures. After an appropriate sterilizing duration, the autoclave was depressurized and cooled. One of the drawbacks of steam autoclave sterilization is that some equipment is damaged by high temperatures and pressures.

The same steam autoclave systems have also been used for sterilizing or disinfecting medical wastes. However, autoclave sterilization is relatively time consuming and expensive, particularly for waste materials.

Instruments and equipment which could not withstand the temperature and pressure of an autoclave were commonly sterilized with ethylene oxide gas. After the equipment was sealed in a sterilizing chamber, the highly toxic ethylene oxide was introduced under pressure and allowed to remain for a few hours, as was appropriate to the selected sterilizing cycle. After the sterilizing cycle, the equipment could not be utilized until the absorbed ethylene oxide was removed. This generally required about 12 to 16 hours in a vacuum or about 72 hours at ambient atmospheric conditions. In addition to the long cycle time, there is also concern with operator safety when working with the highly toxic ethylene oxide gas. Strict safety procedures must be followed to prevent inadvertent venting and breathing of the ethylene oxide gas.

Liquid sterilization systems have been used for equipment which could not withstand the autoclave or ethylene oxide systems. However, prior to the parent applications hereto, most such liquid sterilization was performed manually. The equipment was immersed in a vat or tank which was filled with the sterilizing solution, rinsed, and used. Frequently, non-sterile tap water was used as the rinse. The potential for operator error leads to concerns of sterilization assurance when equipment has been manually sterilized.

Liquid sterilants, such as iodine, have been used in medical waste disposal systems. More specifically, medical wastes have been ground with water to make a more readily disposable slurry. Bound iodine solutions were commonly added manually to kill pathogenic organisms. However, the manual addition of liquid iodine again led to sterilization or disinfection assurance questions.

Perhaps the most common technique for disposing of medical waste including syringes, laboratory equipment, culture medium, and the like has been incineration. The wastes were incinerated at sufficiently high temperatures that the pathogenic organisms were killed. However, incinerators tend to be sources of air pollution. Air pollution restrictions render the construction of new incinerators difficult and in some cases impossible. Because reducing the air pollution from existing incinerators tends to be very expensive and in many cases impossible, older incinerators are being closed.

In the above-referenced U.S. Pat. No. 5,037,623, liquid peracetic acid is stored in a sturdy plastic ampule that has a vent aperture positioned at its volumetric center. The ampule is filled just under half way full such that the surface of the liquid is below the vent aperture in any orientation of the ampule. In this manner, the liquid cannot block access to the vent aperture by vapors and gases in the space above the liquid. A semi-permeable membrane covers the aperture to prevent splashed liquid from escaping. Although successful, this ampule does have the drawback that it is about twice as large as the volume of liquid which it carries.

The present invention contemplates a new and improved packaging system and microbial decontamination procedure.

SUMMARY OF THE INVENTION

In accordance with one aspect of the present invention, a package for liquids which liberate gas or vapor is provided. A cylinder is flattened and sealed at a first end and a pair of vent holes are provided, one adjacent each corner. After the package is substantially filled with the liquid, a second end of the cylinder is flattened and sealed, generally transverse to the first end. Another pair of vent apertures is provided adjacent each corner of the second end. Semi-permeable membranes are disposed between the liquid and each of the vent apertures to restrain the liquid within the container while permitting gas and vapor to pass through a vent aperture in an uppermost position.

In accordance with a more limited aspect of the present invention, the liquid is peracetic acid which decomposes with time to liberate oxygen.

In accordance with another aspect of the present invention, a second package which contains at least buffers and pH adjusting materials is fixed to the first package.

In accordance with a yet more limited aspect of the present invention, the second package includes anti-corrosives for inhibiting the peracetic acid from corroding instruments and equipment.

In accordance with another more limited aspect of the present invention, the second package includes an anti-foam agent and pH buffers which buffer the peracetic acid to a sufficiently high pH that the peracetic acid's half life is reduced to a time comparable with the cycle time of a medical waste grinding unit.

In accordance with another aspect of the present invention, the powder further includes one or more of a deodorizing agent, a fragrance, an indicator to indicate completeness of sterilization, and a colorant.

One advantage of the present invention resides in its low cost.

Another advantage of the present invention resides in its light weight and compactness. High shipping densities are permitted.

Another advantage of the present invention is that it safely vents gases and vapor.

Another advantage of the present invention is that it reduces the potential for operator error by provided prepackaged unit doses.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 3 illustrates the self-vented liquids package in combination with an automatic liquid sterilizing system;

BRIEF DESCRIPTION OF THE PREFERRED EMBODIMENTS

Figure 1A:
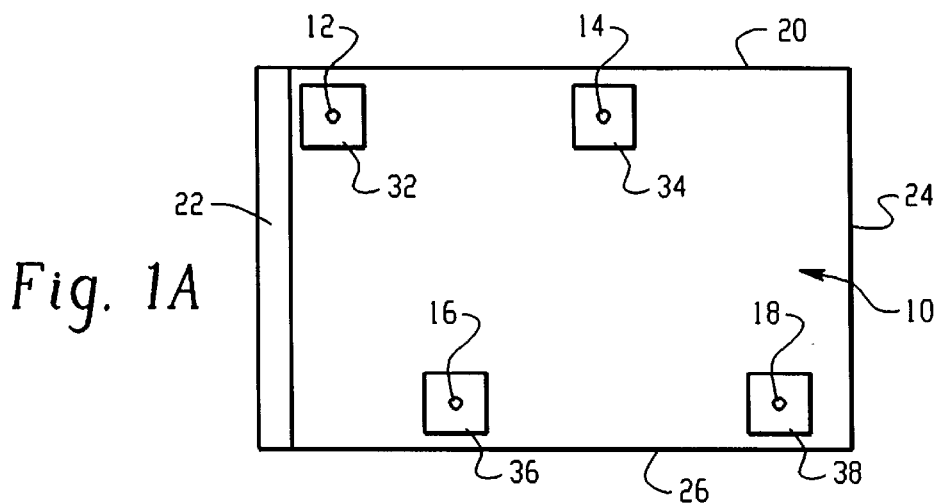
FIGS. 1A, 1B, 1C, 1D, and 1E illustrate a manufacturing process for manufacturing a preferred self-venting liquid package in accordance with the present invention.

With reference to FIGS. 1A–1E, a sheet of flexible stock 10 is punched with a first vent aperture 12, a second vent aperture 14, a third vent aperture 16, and a fourth vent aperture 18. The first vent aperture 12 is disposed along a first edge 20 adjacent a region 22 which is reserved for adhesives or other bonding material. The second vent aperture 14 is disposed along the first edge about half way between the first aperture 12 and an opposite end 24 of the sheet stock. The third vent aperture 16 is disposed adjacent an opposite edge 26 of the card stock mid-way between the first and second apertures. The fourth aperture 18 is disposed adjacent the second longitudinal edge near the second end 24. The sheet stock 10 is preferably a material which is impermeable to strong oxidants, such as peracetic acid. Suitable sheet stock materials include plastic-lined paper, flexible plastic sheet stock, and the like.

Sections of semi-permeable membrane 32, 34, 36, 38 are adhered over each of the first, second, third, and fourth vent apertures 12, 14, 16, 18, respectively. Four individual segments of semi-permeable membrane may be provided as illustrated in FIG. 1A or, a single sheet of semi-permeable membrane material which covers all four vent apertures may be provided for simplicity of manufacture.

Figure 1B:
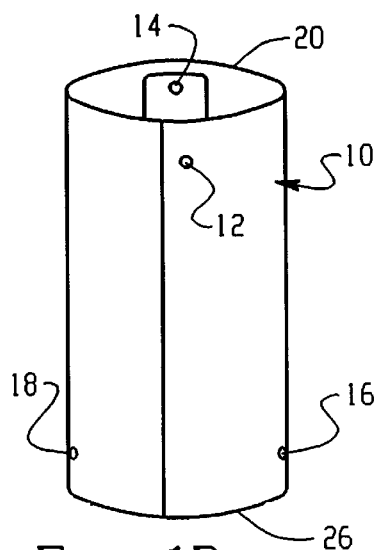

The bonding or lapped portion 22 is lapped over edge 24 as illustrated in FIG. 1B to define a cylinder. Alternately, the cylinder of FIG. 1B may be extruded, which extrusion is followed by the punching of the four apertures 12, 14, 16, and 18. A semi-permeable membrane sleeve or pieces are adhered to the inside of the sleeve covering the four vent apertures.

Figure 1C:
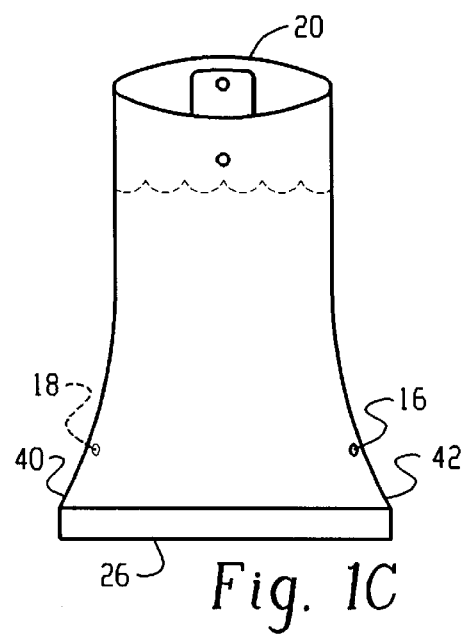
Figure 1D:
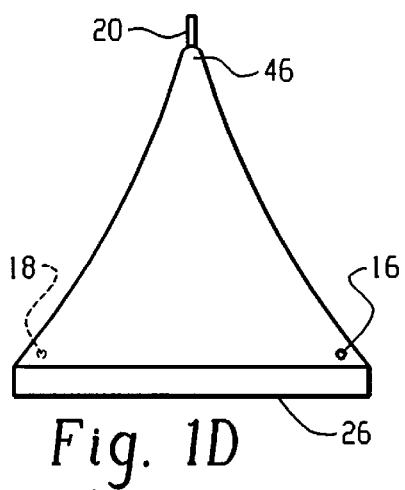

With reference to FIG. 1C, the cylinder is squeezed flat along the second longitudinal edge 26 and sealed such that the third and fourth apertures 16, 18 are disposed adjacent two corners 40, 42 defined by flattening the edge of the cylinder flat. The longitudinal edge 26 is sealed to prevent the escape of liquids. A unit dose of liquid is inserted into the container. With reference to FIG. 1D, the first edge 20 is flattened and sealed in a direction substantially orthogonal to the direction of the second edge 26. This places the first and second vent apertures 12, 14 closely adjacent corners 44, 46 which are defined when the first edge 24 is flattened.

Figure 1E:
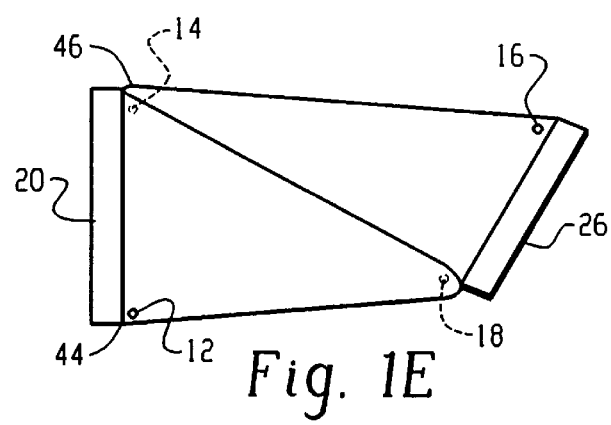

With reference to FIG. 1E, a container A is formed which has four generally triangular sides which define the four orientations which are stable when the structure is laid on a horizontal surface. In each of the four stable orientations, one of the four vents is at or adjacent the uppermost point of the interior volume. Any liberated oxygen or other gases or vapors rise to a small air space at the uppermost portion of the interior volume and are vented through the uppermost vent aperture.

Figure 2A:
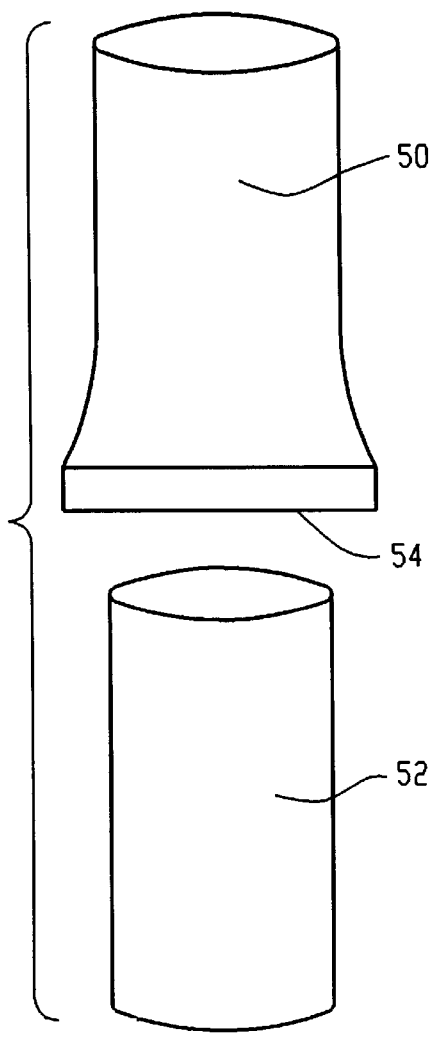
FIGS. 2A, 2B, 2C and 2D illustrate an alternate embodiment for manufacturing the self-venting package.

With reference to FIG. 2A, a sleeve 50 of semi-permeable material is insertable into a sleeve 52 of paper, plastic-lined paper, or plastic material. A first end 54 of the semi-permeable sleeve is sealed and inserted into the exterior sleeve 52.

Figure 2B:
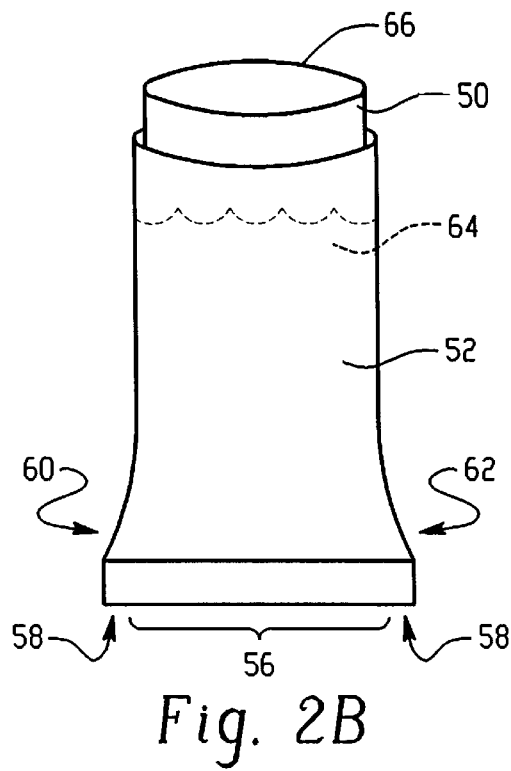
Figure 2C:
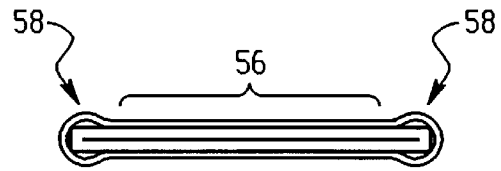
Figure 2D:
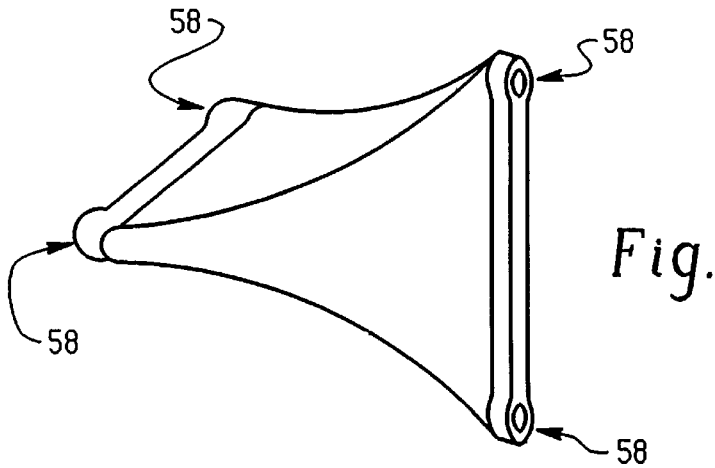

With reference to FIGS. 2B and 2C, the exterior sleeve is flattened and sealed along a central portion 56, e.g. with a staple, folded paper or plastic portion, adhesive, or the like. Portions 58 of the outer sleeve adjacent corners 60, 62 are left unsealed to provide a vent aperture adjacent each corner. A unit dose of the peracetic acid or other liquid 64 is loaded into the impermeable liner. With reference to FIG. 2D, the semi-permeable sleeve 50 is sealed along a top edge 66. The outer liner 52 is flattened along edge 66 and sealed in the center. This again provides a pair of vent apertures 58 adjacent each corner.

With reference to FIG. 3, a liquid sterilizing system includes a water supply line 100 which supplies water to a water sterilizing means 102, such as a membrane filter which removes biological contaminants from the water. A pump 104 selectively pumps the water through a heater 106 to a sterilant and powdered reagent entraining region 108. In the preferred embodiment, powdered reagents are emptied from the container into a well 110 and are dissolved by flowing water. To avoid operator contact with the peracetic acid, a needle inlet end 114 of an aspirator 116 punctures the self-venting container A and aspirates the peracetic acid out of it. Alternately, a cutter may be provided such that the self-vented container is punctured or cut allowing the flowing water to intermix with its contents. The sterilant solution flows through spray nozzle 118 into a sterilizing region 120 and returns through the well 110. Items with hollow interiors are connected with a manifold 122 that sprays the antimicrobial solution into the interior. At the end of the cycle for microbially decontaminating items in the sterilizing region, a drain valve 124 is opened draining the liquid solution from the system. An air sterilizing means 126 such as a filter, removes airborne microbes from the air which is drawn into the sterilizing region to replace the drained liquids.

In a rinse cycle, water flows through the microbe removing filter 102 to remove all pathogenic microbes. The microbe-free rinse is pumped over the items and the sterilizing region to remove any residue. Microbe-free air then replaces the rinse as it is drained.

Figure 4:
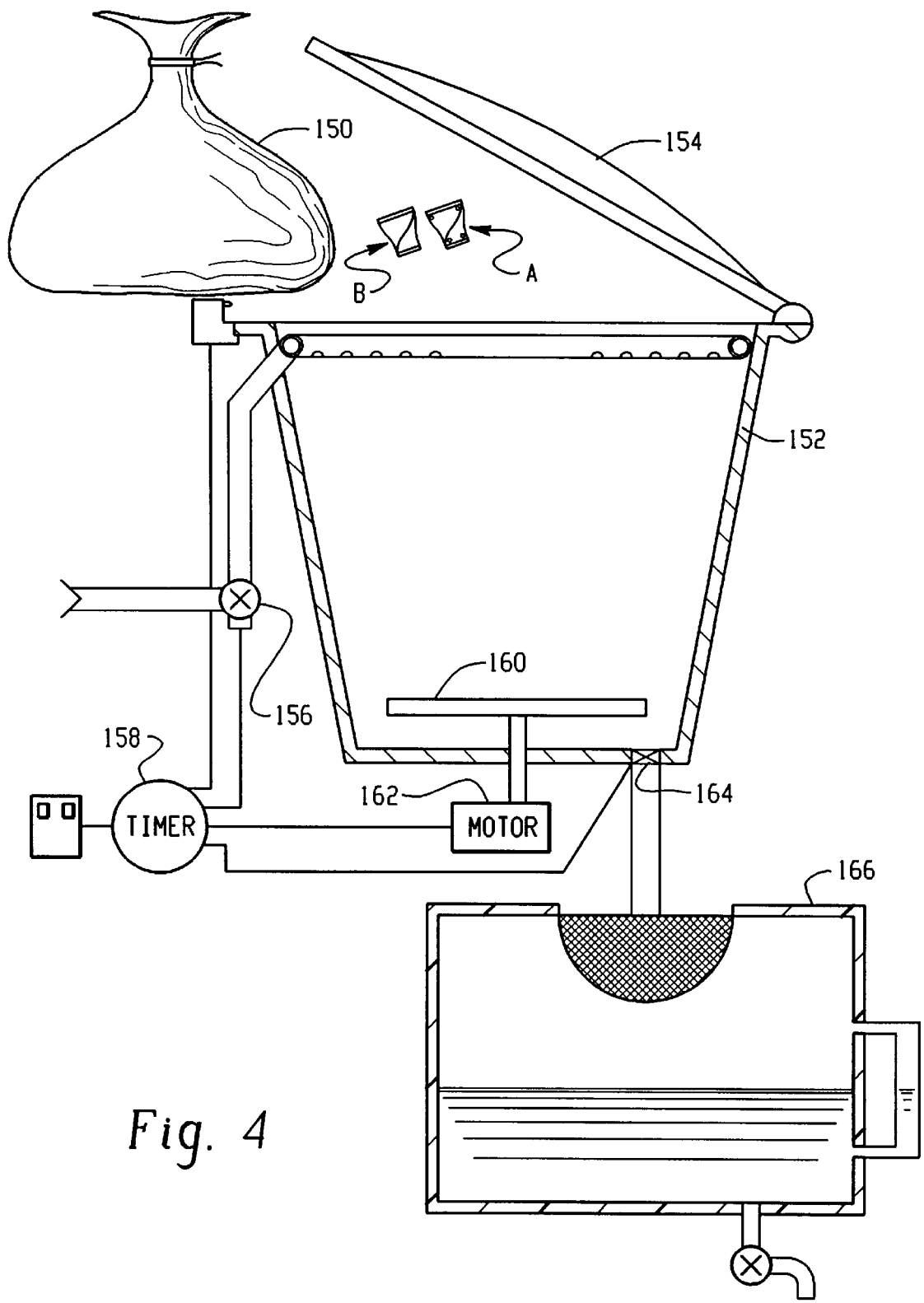
FIG. 4 illustrates the self-vented package in combination with a medical waste grinding and disposal system.

With reference to FIG. 4, the present invention is also usable in conjunction with the decontamination of medical wastes. A plastic bag 150 of medical wastes is placed in a comminuting container 152 along with one of the self-venting containers A. Preferably, a second container B with buffering ingredients are also placed concurrently into the comminuting chamber. A lid 154 is closed and sealed. A water valve 156 under control of a timer 158 introduces a preselected amount of water into the comminution chamber 152. A comminuting means such as a rapidly rotating cutting blade 160 is rotated by a motor 162. At the end of a preselected comminuting cycle, a drain valve 164 is opened allowing the disinfected and comminuted medical wastes to be drained to a waste receptacle 166.

The self-vented container A is preferably attached to a second analogous container B. The second container B contains additional reagents which are appropriate to the specific sterilizing or microbial decontamination application. In the instrument sterilization embodiment of FIG. 3, the container B preferably includes a pH buffer for buffering the pH to near a neutral pH, corrosion inhibitors for inhibiting the peracetic acid from corroding copper, aluminum, brass, steel, and other materials of which medical instruments are commonly made. Preferably, wetting agents or detergent and an anti-foaming agent, are also provided. When the system is to be used with hard water, the container B preferably also contains buffers for preventing calcium and magnesium salts from being deposited on the sterilized instruments and equipment.

In the medical waste decontamination embodiment of FIG. 4, the second container B contains similar ingredients. More specifically, buffers are provided for buffering the peracetic acid. The pH to which the peracetic acid is buffered has a significant affect on its half-life. Accordingly, the second container B includes appropriate pH buffers and adjusters to adjust the pH of the slurry in the comminution chamber 152 to a pH which causes the half-life of the peracetic acid to be commensurate with the duration of the comminution and disposal cycle. A pH in the range of 10–12, well into the basic range, shortens the half-life of the peracetic acid to about 15–45 minutes.

The second container B preferably also contains deodorants, fragrances, anti-foaming agents, and the like. The second or even an additional container may contain a color indicator such as gentian violet which imparts a dark violet color to the slurry. Gentian violet fades to white in the presence of acid. Accordingly, the amount of gentian violet selected is such that the solution turns from purple to white in response to an appropriate concentration of peracetic acid being present to sterilize the slurry. In this manner, if the peracetic acid is for some reason defective, for example if it had been left on the shelf past its marked shelf-life and had decomposed and become too weak to be effective, the slurry would remain purple providing a visual indication to the operator that sterilization or microbial decontamination of the wastes has not been achieved.

In the embodiment of FIG. 4, containers A and B are preferably deposited into the comminution chamber as a unit. The self-vented container A and the second container B are, for example, adhered together with an adhesive, such as rubber cement. For insertion into the sterilizer of FIG. 3, the powdered reagent container is separated, ripped open, and emptied into the well 110. The peracetic acid container is then placed into the well in the appropriate position to be entered by aspiration needle 114 or to be cut by a cutting means.

Figure 5:
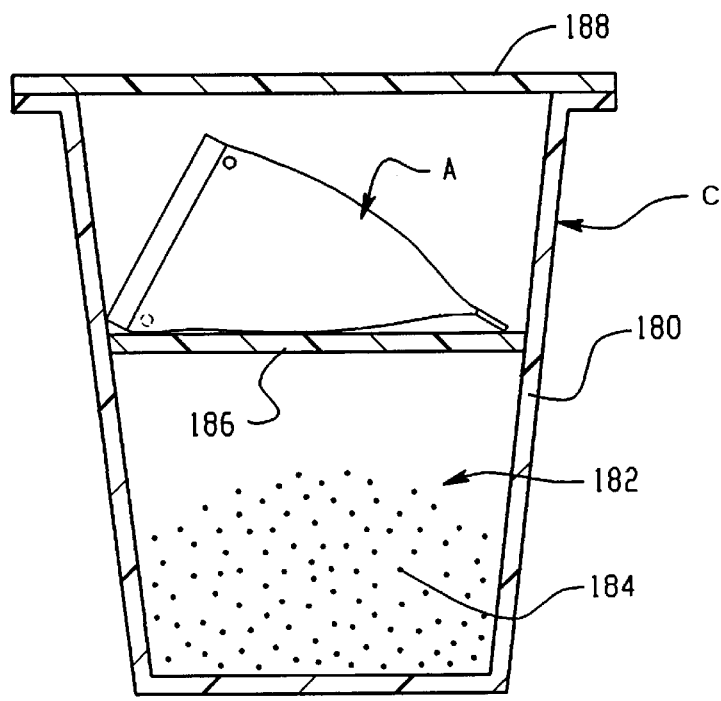
FIG. 5 illustrates a self-venting liquid package in accordance with the present invention in combination with a package for carrying dry reagents; and, FIG. 6 illustrates another alternate embodiment in which a self venting liquids package is integrally connected with a package for other reagents to insure that both are used together.

Various means are contemplated for affixing the two containers together. As illustrated in FIG. 5, a plastic cup 180, analogous to a drinking cup C, may be defined with a lower compartment 182 which receives the powdered reagents 184. A shelf or divider 186 provides a support for the self-vented container A. A cover or lid 188 having a slit or vent for the liberated gases or vapors closes the container.

Figure 6:
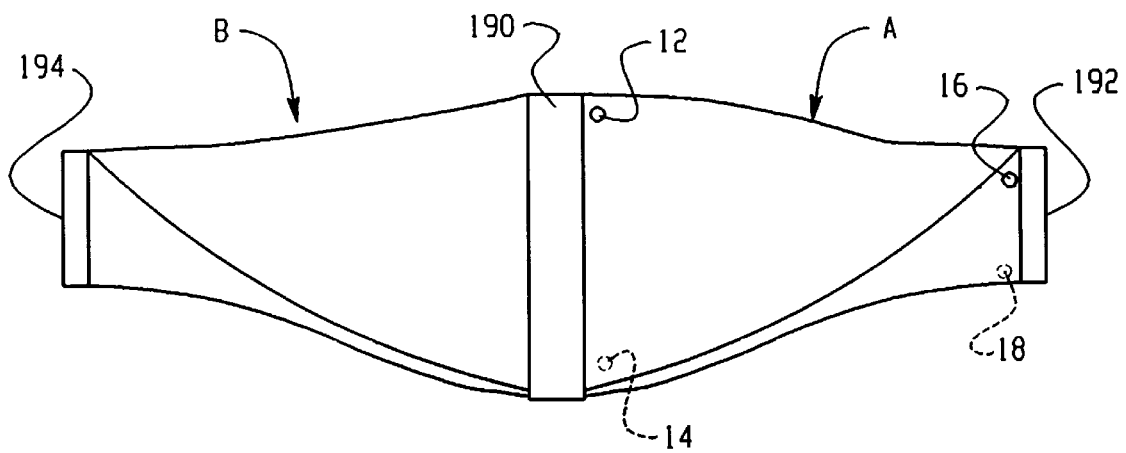

With reference to FIG. 6, the containers A and B are integrally connected. A single tube which has vent apertures 12, 14, 16, 18 towards one end is flattened and sealed centrally 190. The end with the vent apertures is filled with a liquid, flattened, and sealed at a far end 192 to form the self-vented container. The other end is filled with the powdered reagent, flattened and sealed at the opposite end 194 to form the other container B. Connecting the two containers together integrally helps assure that the two will always be used as a unit and reduces the possibilities for operator error.

Optionally, because the semi-permeable membrane may tend to allow fluid to wick therethrough if it contacts other associated structures, a means may be provided for holding associated structures away from the semi-permeable membrane. In the embodiment of FIG. 6, a raised annular rib surrounds each of the vent apertures. These ribs may be formed by embossing an extruded plastic tube or flat sheet stock when the vent apertures are punched.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A self-venting container for simultaneously holding liquids and venting gas or vapor, the container comprising:
   a generally tubular body portion which is flattened at a first end in a first direction and sealed, and which is flattened at a second end in a second direction generally perpendicular to the first direction and sealed, such that four corners are defined adjacent ends of the first and second ends;
   four vent apertures, each vent aperture defined closely adjacent one of the corners;
   semi-permeable membrane portions covering an interior of each of the vent apertures, the semi-permeable material portions retaining liquids while allowing gases and vapors to pass therethrough.

2. The container as set forth in claim 1 wherein the vent apertures are holes punched in the generally tubular body portion.

3. The container as set forth in claim 2 wherein the semi-permeable membrane portions include four distinct segments of semi-permeable membrane material each adhered to an inner surface of the body portion surrounding each of the vent apertures.

4. The container as set forth in claim 1 wherein the semi-permeable material portions are integrally in a semi-permeable material sleeve which surrounds a defined interior volume of the body portion.

5. The container as set forth in claim 1 further including a liquid substantially filling an interior volume thereof such that three of the vent apertures are below liquid level and at least one vent aperture is above liquid level in any orientation, whereby the vent aperture above the liquid level permits gas and vapor liberated from the liquid to pass therethrough.

6. The container as set forth in claim 5 wherein the liquid includes peracetic acid and wherein the gas or vapor liberated by the liquid includes oxygen gas.

7. The container as set forth in claim 6 in combination with a second container which contains reagents that interact with the peracetic acid to promote microbial decontamination.

8. The container as set forth in claim 7 wherein the second container reagents include buffers for controlling pH.

9. The container as set forth in claim 8 wherein the second container reagents further include corrosion inhibitors and wetting agents.

10. The container as set forth in claim 8 wherein the second container reagents include anti-foaming agents, and at least one of a deodorizer and a fragrance.

11. The container of claim 10 in combination with a grinder for grinding biological wastes and for grinding the containers to release the peracetic acid and microbially decontaminate the biological wastes.

12. The container as set forth in claim 6 wherein the second container includes:

a generally tubular body portion which is flattened at a first end in a first direction and sealed and flattened at a second end in a second direction generally orthogonal to the first direction and sealed.

13. The container as set forth in claim 12 wherein the first end of the second container and the second end of the first container are integrally connected.

14. The container as set forth in claim 6 in combination with an automated microbial decontamination system which includes:

a means for releasing the peracetic acid from the container and mixing the peracetic acid with water to form an anti-microbial solution;

a means for circulating the anti-microbial solution over to be microbially decontaminated;

a rinse means for rinsing the microbially decontaminated with a pathogenic microbe free rinse.

15. A method comprising:

defining a cylinder which has oppositely disposed first and second vent apertures adjacent a first end and has oppositely disposed third and fourth vent apertures adjacent a second end, the first and second vent apertures being 90° offset from the third and fourth vent apertures;

lining the vent apertures with semi-permeable material which permits gases to pass therethrough but which restrains liquids from passing;

closing the first end of the cylinder in a flat sealed edge to define corners at opposite ends thereof, the first and second vent apertures being disposed closely adjacent the first and second corners;

depositing a unit measure of a liquid in the cylinder portion;

closing the second end in a flat sealed edge to define third and fourth corners at opposite ends thereof, the third and fourth vent apertures being disposed adjacent the third and fourth corners.

16. The method as set forth in claim 15 wherein the liquid includes a strong oxidant.

17. The method as set forth in claim 16 wherein the strong oxidant includes peracetic acid.

18. The method as set forth in claim 16 further including:

placing the cylinder with the sealed edges unopened and biological wastes in a comminuting chamber;

adding a measured volume of a liquid to the comminuting chamber;

comminuting the biological wastes and the container into a slurry of water and fine particulates, the comminuting releasing the strong oxidant such that the strong oxidant kills microbial decontaminants in the wastes and the slurry.

19. The method as set forth in claim 18 further including:

filling a second package with a pH buffer, an anti-foaming agent, and at least one of a deodorant and a fragrance;

interconnecting the second package with the first cylinder prior to placing the first cylinder into the comminuting chamber such that the first and second packages are inserted unopened into the comminuting chamber as a unit.

20. The method as set forth in claim 16 further including:

puncturing the cylinder, withdrawing the strong oxidant, and intermixing the withdrawn strong oxidant with water to form an anti-microbial solution;

circulating the anti-microbial solution over items to be microbially decontaminated;

draining the anti-microbial solution;

rinsing the items with a microbe-free rinse.

* * * * *